United States Patent
Igaki et al.

(10) Patent No.: US 10,231,852 B2
(45) Date of Patent: Mar. 19, 2019

(54) VASCULAR STENT

(71) Applicant: KYOTO MEDICAL PLANNING CO., LTD., Kyoto (JP)

(72) Inventors: Keiji Igaki, Kyoto (JP); Hirokazu Yamada, Kyoto (JP); Mitsuhiko Kinoshita, Kyoto (JP)

(73) Assignee: KYOTO MEDICAL PLANNING CO., LTD., Kyoto (JP)

( * ) Notice: Subject to any disclaimer, the term of this patent is extended or adjusted under 35 U.S.C. 154(b) by 1 day.

(21) Appl. No.: 15/100,555

(22) PCT Filed: Dec. 3, 2014

(86) PCT No.: PCT/JP2014/081992
§ 371 (c)(1),
(2) Date: May 31, 2016

(87) PCT Pub. No.: WO2015/098443
PCT Pub. Date: Jul. 2, 2015

(65) Prior Publication Data
US 2016/0296354 A1    Oct. 13, 2016

(30) Foreign Application Priority Data
Dec. 25, 2013 (JP) ................................. 2013-266283

(51) Int. Cl.
*A61F 2/88* (2006.01)
*A61F 2/90* (2013.01)
(Continued)

(52) U.S. Cl.
CPC .................. *A61F 2/88* (2013.01); *A61F 2/90* (2013.01); *A61F 2/915* (2013.01);
(Continued)

(58) Field of Classification Search
CPC ...... A61F 2/82; A61F 2/88; A61F 2/89; A61F 2/90; A61F 2/915; A61F 2002/9155;
(Continued)

(56) References Cited

U.S. PATENT DOCUMENTS 5,133,732 A * 7/1992 Wiktor ...................... A61F 2/88
604/104
5,824,059 A * 10/1998 Wijay ...................... A61F 2/90
623/1.15
(Continued)

FOREIGN PATENT DOCUMENTS

EP    1 813 231    8/2007
EP    2 301 486    3/2011
(Continued)

OTHER PUBLICATIONS

International Search Report issued in PCT/JP2014/081992, 2 pages.
(Continued)

*Primary Examiner* — Seema Mathew
(74) *Attorney, Agent, or Firm* — K&L Gates LLP (57) ABSTRACT

A vascular stent (1) for scaffolding a vessel (11) from the inside, wherein the stent is provided with a plurality of tube-forming elements (3A), (3B), and (3C) for forming a tube (2), the tube-forming elements combining with each other to construct a single flow path. Each of the tube-forming elements is formed by bending a strand comprising a single continuous biodegradable polymer, and first and second projecting parts (4, 5) are formed by successive alternation. Formation occurs in multiple stages in the axial direction of the tube by connecting using connecting legs (6) for successively connecting one side of the first projecting part and the other side of the second projecting part where the first and second projecting parts successively alternate. Elastic displacement parts (9) for performing elastic displacement by applying a pressing force to the tube are
(Continued)

formed in the middle of the connecting legs successively connecting the first and second projecting parts of the tube-forming elements.

6 Claims, 9 Drawing Sheets

(51) Int. Cl.
  *A61F 2/30* (2006.01)
  *A61F 2/95* (2013.01)
  *A61F 2/915* (2013.01)
(52) U.S. Cl.
  CPC ............... *A61F 2002/30329* (2013.01); *A61F 2002/9511* (2013.01); *A61F 2210/0004* (2013.01); *A61F 2220/005* (2013.01); *A61F 2220/0058* (2013.01); *A61F 2250/006* (2013.01)
(58) Field of Classification Search
  CPC ............ A61F 2002/91583; A61F 2/885; A61F 2/852; A61F 2/86; A61F 2002/91508; A61F 2002/91533; A61F 2002/30329; A61F 2002/9511
  See application file for complete search history.

(56) References Cited

U.S. PATENT DOCUMENTS

| | | | | |
|---|---|---|---|---|
| 6,017,365 A * | 1/2000 | Von Oepen | ............... | A61F 2/88 623/1.15 |
| 6,059,808 A * | 5/2000 | Boussignac | ............... | A61F 2/88 606/191 |
| 6,068,656 A * | 5/2000 | Von Oepen | ............... | A61F 2/91 623/1.15 |
| 6,165,213 A * | 12/2000 | Goicoechea | ............. | A61F 2/07 623/1.11 |
| 6,805,704 B1 * | 10/2004 | Hoyns | ........................ | A61F 2/91 623/1.15 |
| 7,637,935 B2 * | 12/2009 | Pappas | ....................... | A61F 2/91 623/1.12 |
| 9,078,748 B2 * | 7/2015 | Paul | ....................... | A61F 2/2412 |
| 2001/0010015 A1 * | 7/2001 | Hijlkema | .................. | A61F 2/86 623/1.16 |
| 2004/0024444 A1 * | 2/2004 | Moore | .................... | A61F 2/915 623/1.15 |
| 2006/0004436 A1 | 1/2006 | Amarant et al. | | |
| 2010/0198333 A1 * | 8/2010 | Macatangay | ............. | A61F 2/07 623/1.15 |
| 2011/0213455 A1 * | 9/2011 | Obradovic | ................ | A61F 2/07 623/1.15 |
| 2012/0165921 A1 * | 6/2012 | Casey | ..................... | A61F 2/915 623/1.16 |

FOREIGN PATENT DOCUMENTS

| | | |
|---|---|---|
| JP | 2003531673 | 10/2003 |
| JP | 2005046648 | 2/2005 |
| JP | 2008208989 | 3/2008 |
| WO | 2006051912 | 5/2006 |

OTHER PUBLICATIONS

Extended European Search Report dated Jul. 12, 2017 in corresponding European Application No. 14874716.5.

* cited by examiner

VASCULAR STENT

CROSS REFERENCE TO RELATED APPLICATIONS

The present application is a National Stage of International Application No. PCT/JP2014/081992 filed Dec. 3, 2014 and which claims priority to Japanese Patent Application No. JP2013-266283 filed Dec. 25, 2013, the entire contents of which are being incorporated herein by reference.

BACKGROUND

Technical Field

The present disclosure relates to a vascular stent for implanting within a vessel of a living body such as a blood vessel, trachea or bile duct to scaffold the lumen of the vessel from the inside.

Background Art

Heretofore, in a vessel of a living body, particularly in the case of stenosis occurring in a blood vessel such as a coronary artery, percutaneous transluminal angioplasty (PTA) has been performed in which a balloon catheter is used to expand the stenosed portion from the inside to improve blood flow.

The site once stenosed, however, is known to have a high probability of restenosis or acute occlusion due to intimal dissection even after PTA. To prevent such acute occlusion or restenosis, a tubular shaped stent is implanted at the site following PTA. The stent used herein is in a contracted state when introduced into a blood vessel, and subsequently expanded in diameter so as to be deployed at the intended site to scaffold the vessel from the inside to maintain an open state.

This variety of vascular stent is inserted to the target lesion within the blood vessel in the contracted state along with a stent delivery device such as a catheter. Once the vascular stent is inserted at the lesion, an expanding mechanism such as a balloon provided in the stent delivery device is used for expansion thereof from the contracted state into an expanded state and the blood vessel is scaffolded in an expanded state.

Thus, all conventionally used and heretofore proposed vascular stents have been configured to change from a contracted state to an expanded state.

Vascular stents have been proposed which are configured to enable changing from a contracted state to an expanded state in which ring-shaped strands having zig-zag bends are connected by a connecting part as a tubularly shaped (PLT 1 and 2).

Furthermore, the applicant of the present application has proposed a vascular stent configured to have a single flow path from one side to another side in which a strand made of a biodegradable polymer is bent so as to have successively alternating straight portions and bent portions to form a tube-forming element, a plurality of which are combined together to each form a portion of a tube (PLT 3 and 4).

CITATION LIST

Patent Literature

PLT 1: Japanese Unexamined Patent Application Publication No. 2005-348813
PLT 2: Japanese Unexamined Patent Application Publication No. 2005-349204
PLT 3: WO2006/051912
PLT 4: WO2009/157164

SUMMARY

Technical Problem

In order to prevent restenosis or acute occlusion due to intimal dissection at the PTA site, the interior of a blood vessel is desirably scaffolded in a state of uniform expansion by implanting a stent at the stenosed site. Uniformly expanding the inner wall of the blood vessel with the stent suppresses intimal dissection at the implant site, achieves smooth blood flow and suppresses retention of foreign objects such as thrombi.

However, it is known that stenosis of blood vessels occurs due to atheromata caused by arterial hardening or due to foreign objects such as thrombi accumulating on inner walls of blood vessels. In such a stenosed site in a blood vessel, hyperplasia occurs in irregular shapes and partially.

Accordingly, because the stenosed site of the blood vessel expanded and scaffolded from the inside by the vascular stent has an irregularly shaped and partially occurring hyperplasia, it is desirable to scaffold the stenosed site while changing shape to conform to hyperplasia occurring in the intima of the blood vessel in order to uniformly expand and scaffold the inner wall of the vessel. Thus, in the vascular stent implanted in the stenosed site of the blood vessel having an irregularly shaped and partially occurring intimal hyperplasia, during pulsation of the blood vessel, load is concentrated in portions where the irregularly shaped hyperplasia is scaffolded and in its vicinities.

In heretofore proposed vascular stents having connected parts or bonded parts of strands such as vascular stents having connected ring-formed strands and vascular stents comprising tube-forming elements formed from a strand of a biodegradable polymer having connected parts or bonded parts in the strand, when load is concentrated in the connected or the bonded parts of the strand, damage such as bending of the connected or the bonded parts leads to difficulty in uniformly expanding and scaffolding the interior of the blood vessel and it might not be possible to correctly scaffold the blood vessel in an open state.

An object of the present disclosure is to provide a vascular stent which, even in the case of stenosis with partial and irregularly shaped hyperplasia occurring in a vessel such as a blood vessel, can uniformly expand and scaffold the vessel from the inside.

Another object of the present disclosure is to provide a vascular stent which, when implanted into a vessel such as a blood vessel, even in the case of a load being concentrated in a portion thereof, can absorb this load and can uniformly expand and scaffold the vessel having the stenosed site from the inside.

Yet another object of the present disclosure is to provide a vascular stent which, when implanted into a vessel such as a blood vessel, even in the case of a load being concentrated in a portion thereof, can suppress concentration of the load in connected parts or bonded parts of the strand to prevent such damage as bending of connected parts or bonded parts and stably scaffold the interior of the vessel.

Solution to Problem

To achieve the above-mentioned objects, the present disclosure provides a vascular stent for implanting within a vessel of a living body for scaffolding the vessel from the inside thereof, the vascular stent having a plurality of tube-forming elements which combine with each other to construct a tube constituting a single flow path from one side to another side. These tube-forming elements are formed by bending a strand made of a single continuous biodegradable polymer and, in a middle portion of the strand, a first projecting part bent to project in one direction and a second projecting part bent to project in a direction opposite to the direction of the first projecting part are formed in a plurality of alternating stages. A connecting leg is formed for connecting one side of the first projecting part to another side of the second projecting part where the first projecting part and the second projecting part successively alternate. In the plurality of tube-forming elements, along with being combined by bringing the connecting legs of different tube-forming elements into mutual adjacency, at least a portion of the mutually adjacent connecting legs thereof are bonded to be integrated so that the first and the second projecting parts are disposed in multiple stages alternating in the axial direction of the tube. Furthermore, the tube-forming element has an elastic displacement part provided in a middle portion of the connecting leg thereof for being elastically displaced by a pressing force applied to the tube.

The elastic displacement part provided in a middle portion of the connecting leg of the tube-forming element comprises a pair of bends formed by bending a portion of the single continuous strand in mutually opposite directions.

Furthermore, the elastic displacement part may be formed by curving a portion of the single continuous strand in an approximately s-shape with no mutual overlap.

Still further, the elastic displacement part formed in the tube-forming element is disposed between the first projecting part and the second projecting part of another tube-forming element and yet another tube-forming element when the plurality of tube-forming elements are mutually combined and integrated to constitute the tube.

The strand constituting the tube-forming element is preferably made of one or more biodegradable polymers including polyactic acid (PLA), polyglycolic acid (PGA), copolymer of polyglycolic acid and polyactic acid, polydioxanone, copolymer of trimethylene carbonate and glycolide and copolymer of polyglycolic acid or polylactic acid and ε-caprolactone.

Furthermore, mutually adjacent connecting legs of the plurality of tube-forming elements are bonded in at least a portion thereof by an adhesive agent or by spot welding to be integrated.

The first and the second projecting parts of the tube-forming elements are used as displacing parts to contract and/or expand the outer diameter of the single tube.

Advantageous Effects of Invention

The vascular stent according to the present disclosure, when implanted within a vessel, even in the case of a load being concentrated in a portion thereof, can absorb this load with the elastic displacement part formed in a portion of the tube-forming elements and, in a vessel such as a blood vessel, even in the case of implantation in a stenosed site having partial and irregularly shaped hyperplasia, can uniformly expand and scaffold the vessel from the inside.

Furthermore, the vascular stent according to the present disclosure, by uniformly expanding and scaffolding the vessel from the inside, can achieve smooth blood flow and suppress the occurrence of acute occlusion due to intimal dissection or restenosis.

Still further, in the vascular stent according to the present disclosure, load-concentration in portions is prevented when implanted within a vessel which prevents damage to the vessel caused by load-concentration in connected parts or bonded parts of the tube-forming elements, thereby stably scaffolding the interior of the vessel.

DETAILED DESCRIPTION

Embodiments of the vascular stent according to the present disclosure will now be described with reference to the drawings.

As illustrated in FIGS. 1 to 4, a vascular stent 1 according to this embodiment, for example of the type used for implantation into a coronary artery in a living body, includes a tube 2 constituting a single flow path from one side to another side.

Size of the vascular stent according to the present disclosure can be selected as appropriate according to the vessel of the living body targeted for implantation. For example, in the case of forming the vascular stent 1 for implantation into a coronary artery, size may be an outer diameter R1 of 2 to 5 mm and a length L1 of 10 to 40 mm (refer to FIG. 2). This size is the size of the interior of the vessel when implanted within a vessel of a living body and this size may be selected as appropriate according to the vessel targeted for implantation.

The tube 2 constituting the vascular stent 1 according to this embodiment is formed by combining and integrating a plurality of tube-forming elements 3 formed by bending a single strand comprising a continuous biodegradable polymer.

In this embodiment, as illustrated in FIGS. 1 to 4, the tube 2 is formed by combining three tube-forming elements 3A, 3B and 3C. When these first to third tube-forming elements 3A, 3B, 3C combine with each other to form the single tube 2, each of the tube-forming elements constitute a one third portion of this tube 2.

A biodegradable polymer is used to form the strand constituting the tube-forming element 3 so as not to have adverse effect on a living body such as a human body after implantation. Usable biodegradable polymers include polyactic acid (polylactide: PLA), polyglycolic acid (PGA), polyglactin (copolymer of polyglycolic acid and polylactic acid), polydioxanone, polyglyconate (copolymer of trimethylene carbonate and glycolide) and copolymer of polyglycolic acid or polylactic acid and ε-caprolactone, among others. In addition, a biodegradable polymer of two or more of these materials in a combination may be used.

Particularly, in view of safety in living bodies, it is desirable to use poly-L-lactide (PLLA) for this biodegradable polymer.

Furthermore, a single continuous monofilament of a biodegradable polymer or a multifilament of a plurality of integrated monofilaments may be used to form the strand used to construct the tube-forming element 3. These monofilaments and multifilaments can, for example, be obtained by melt spinning a biodegradable polymer with a melt spinning machine. Selection between using a monofilament and using a multifilament can be made in accordance with such properties as strength and degradation time of the material used in the strand.

The first, second and third tube-forming elements 3A, 3B, 3C will now be described in further detail.

Figure 5:
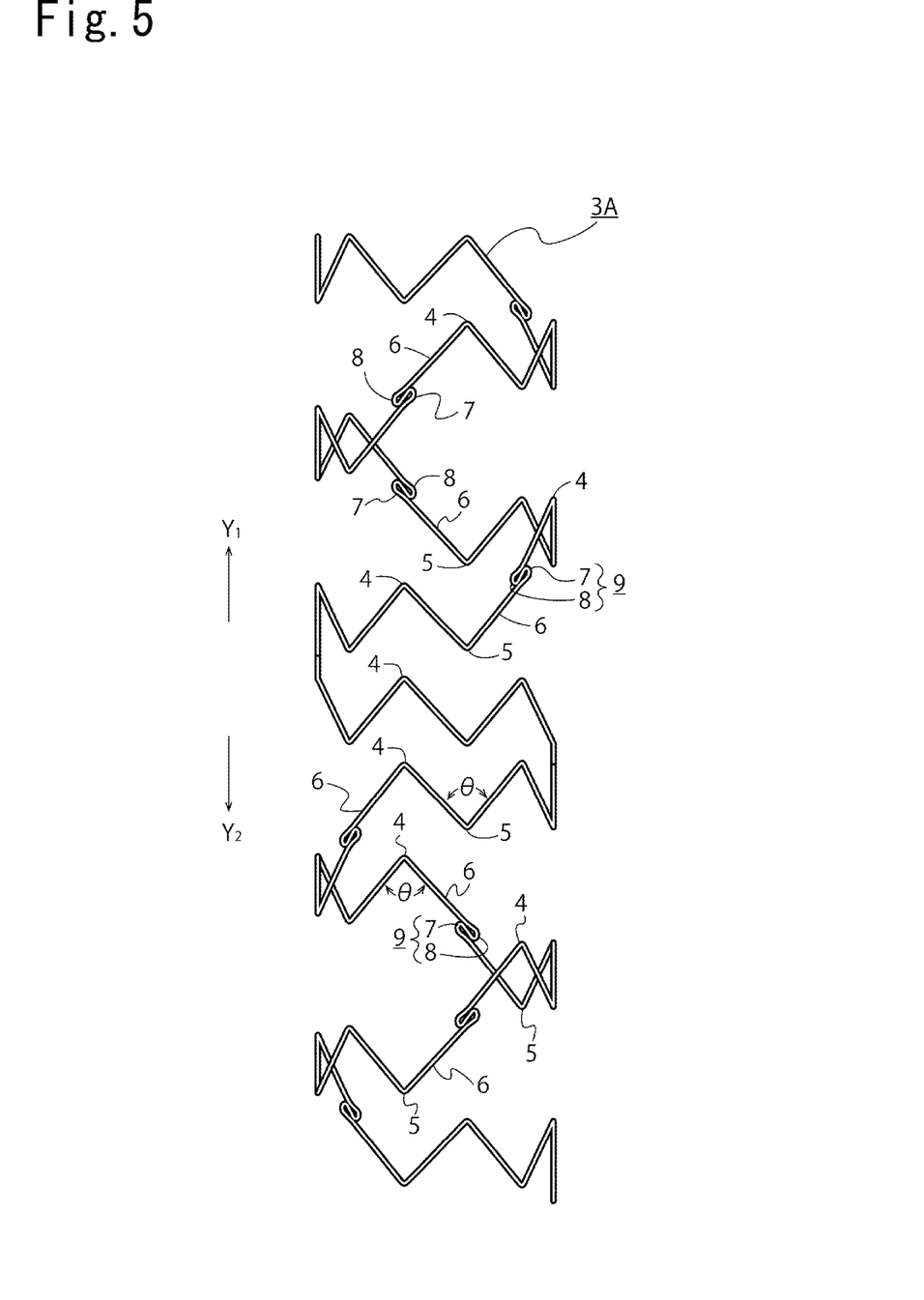
FIG. 5 is a side view illustrating a first tube-forming element for forming the vascular stent illustrated in FIG. 1.

In describing the first tube-forming element 3A, as illustrated in FIG. 5, an alternating plurality of a first projecting part 4 bent so as to project in one direction Y1 as indicated in the drawing and a second projecting part 5 bent so as to project in an opposite direction Y2 as indicated in the drawing are formed in this first tube-forming element 3A. In the example illustrated in FIG. 5, the first projecting part 4 is formed by an upward bending of the strand and the second projecting part 5 is formed by a downward bending of the strand. These first and second projecting parts 4, 5 are formed so as to be disposed in multiple alternating stages in the axial direction of the tube 2 when the tube-forming element 3A is combined with the tube-forming elements 3B and 3C to form the single tube 2.

In the first tube-forming element 3A, where the first projecting part 4 and the second projecting part 5 successively alternate, by forming a connecting leg 6 for successively connecting one side of the first projecting part 4 to another side of the second projecting part 5, the first projecting part 4 and the second projecting part 5 are formed in multiple stages in the axial direction of the tube 2. In this embodiment, the upward-bending first projecting part 4 and the downward-bending second projecting part 5 are formed in alternating two-pair sets which are connected by a connecting leg 6 for successively connecting the one side of the first projecting part 4 to the other side of the second projecting part 5, the connecting leg 6 being formed following the first and second projecting part 4, 5 of these two-pair sets. By connecting the one side of the first projecting part 4 and the second projecting part 5 with the connecting leg 6 formed following the first and second projecting parts 4, 5 of two pairs, the first and second projecting parts 4, 5 are formed in two-pair sets in multiple stages in the axial direction of the tube 2 to form the tube-forming element 3A.

Furthermore, in a middle portion of the connecting leg 6 for connecting the one side of the projecting part 4 to the other side of the projecting part 5, a pair of bends 7, 8 are formed which are curved in mutually opposite directions. These bends 7, 8 are formed by curving a portion of the connecting leg 6 in a direction opposite to the direction in which the first projecting part 4 and the second projecting part 5 succeed so as to be approximately s-shaped together.

As will be described hereinafter, the bends 7, 8 formed by curving a portion of the connecting leg 6 to form an approximate s-shape together constitute an elastic displacement part 9 for being elastically displaced by a pressing force applied to the tube 2 when the tube-forming element 3A is combined with the other tube-forming elements 3B, 3C to constitute the single tube 2.

It should be noted that, in the tube-forming element 3A formed by bending a single continuous strand, shape changes occur due to changing bend shapes to alter the angle θ of bends in the first and second projecting parts 4, 5.

Figure 6:
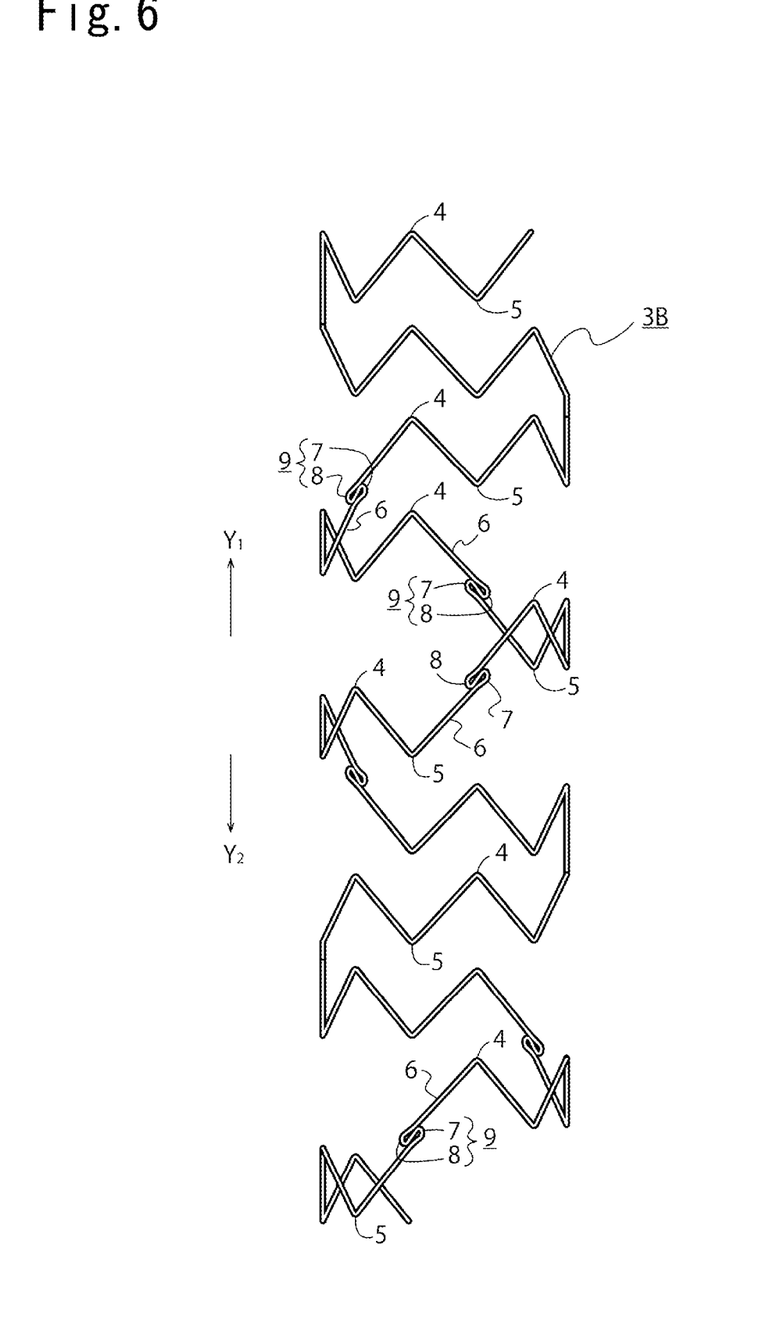
FIG. 6 is a side view illustrating a second tube-forming element for forming the vascular stent illustrated in FIG. 1.

Furthermore, the second tube-forming element 3B, in the same manner as in the first tube-forming element 3A, is also formed by bending a single continuous strand as illustrated in FIG. 6 and, by forming the connecting leg 6 for successively connecting one side of the first projecting part 4 and the other side of the second projecting part 5 where the upward-bending first projecting part 4 and the downward-bending second projecting part 5 successively alternate, the first projecting part 4 and the second projecting part 5 are formed in multiple stages in the axial direction of the tube 2. Furthermore, in a middle portion of the connecting leg 6 for connecting the one side of the projecting part 4 to the other side of the projecting part 5, a pair of bends 7, 8 which are curved in mutually opposite directions are formed. These bends 7, 8 are also formed by curving a portion of the connecting leg 6 in a direction opposite to the direction in which the first projecting part 4 and the second projecting part 5 succeed so as to be approximately s-shaped together. When this tube-forming element 3B is combined with the other tube-forming elements 3A, 3C to constitute the single tube 2, these bends 7, 8 also constitute an elastic displacement part 9 for being elastically displaced by a pressing force applied to the tube 2.

The first and second projecting parts 4, 5 formed in the second tube-forming element 3B are also formed so as to be disposed in multiple stages in the axial direction of the tube 2 when the second tube-forming element 3B is combined with the first and third tube-forming elements 3A, 3C to constitute the single tube 2.

Figure 7:
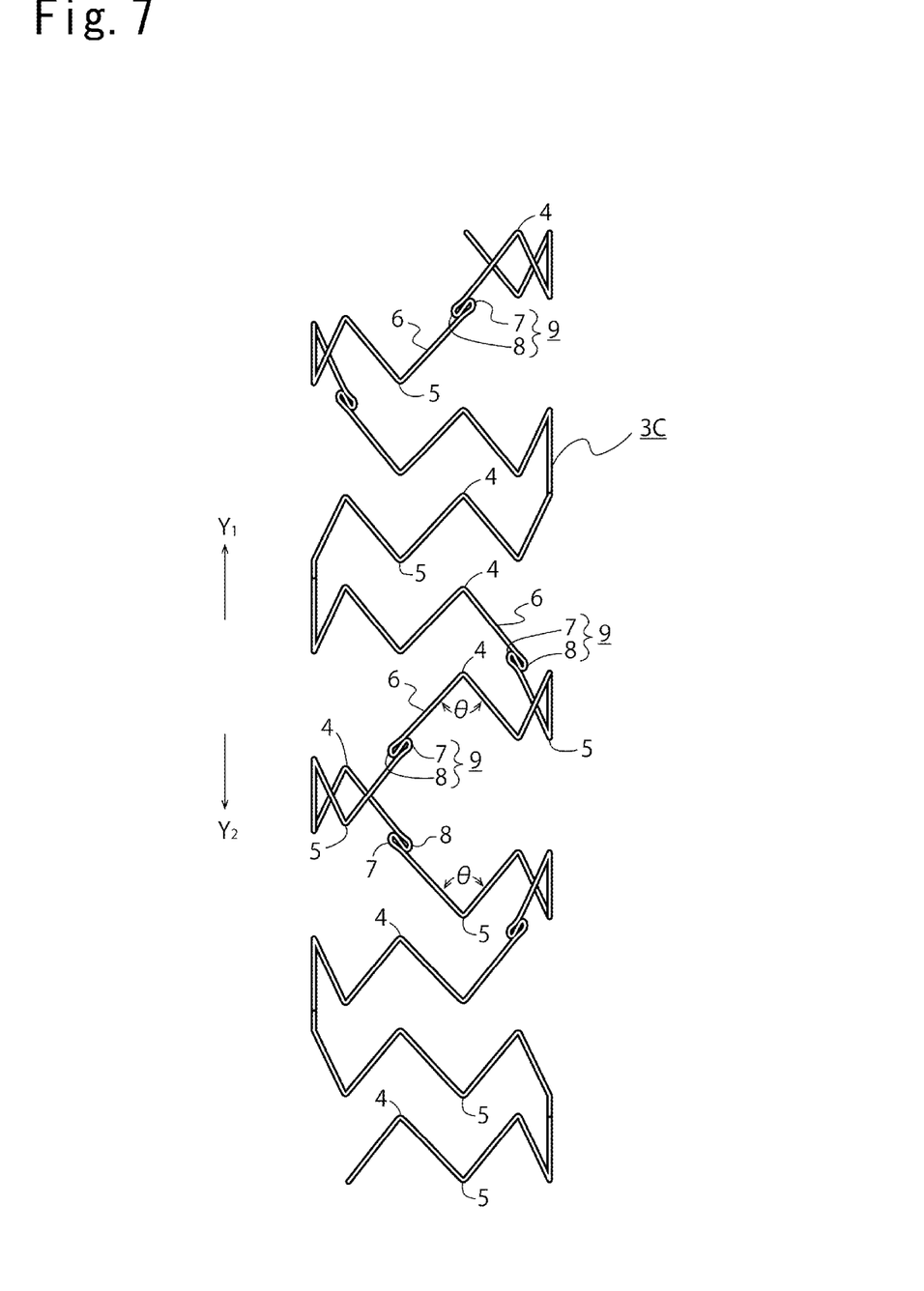
FIG. 7 is a side view illustrating a third tube-forming element for forming the vascular stent illustrated in FIG. 1.

Still further, the third tube-forming element 3C, in the same manner as in the first and second tube-forming element 3A, 3B, is also formed by bending a single continuous strand as illustrated in FIG. 7 and, where the upward-bending first projecting part 4 and the downward-bending second projecting part 5 successively alternate, by forming the connecting leg 6 for successively connecting one side of the first projecting part 4 and the other side of the second projecting part 5, the first projecting part 4 and the second projecting part 5 are formed in multiple stages in the axial direction of the tube 2. Furthermore, in a middle portion of the connecting leg 6 for connecting the one side of the projecting part 4 to the other side of the projecting part 5, a pair of bends 7, 8 which are curved in mutually opposite directions are formed. These bends 7, 8 can also be formed by curving a portion of the connecting leg 6 in a direction opposite to the direction in which the first projecting part 4 and the second projecting part 5 succeed so as to be approximately s-shaped together. When this tube-forming element 3C is combined with the other tube-forming elements 3A, 3B to constitute the single tube 2, these bends 7, 8 also constitute an elastic displacement part 9 for being elastically displaced by a pressing force applied to the tube 2.

The first and second projecting parts 4, 5 formed in the third tube-forming element 3C are also formed so as to be disposed in multiple stages in the axial direction of the tube 2 when the third tube-forming element 3B is combined with the first and second tube-forming elements 3A, 3B to constitute the single tube 2.

The pair of bends 7, 8 constituting the elastic displacement member 9 formed in each of the first to third tube-forming elements 3A, 3B, 3C are formed so as to be located in a middle portion of the connecting leg 6 for connecting the first projecting part 4 and the second projecting part 5 located in upper and lower positions.

When the first to third tube-forming elements 3A, 3B, 3C are combined with each other to form the single tube 2, each constitute a one third portion of the tube 2. Furthermore, the first and second projecting parts 4, 5 formed in multiple stages in each of the tube-forming elements 3A, 3B, 3C are formed with a 120 degree offset for each stage.

Figure 1:
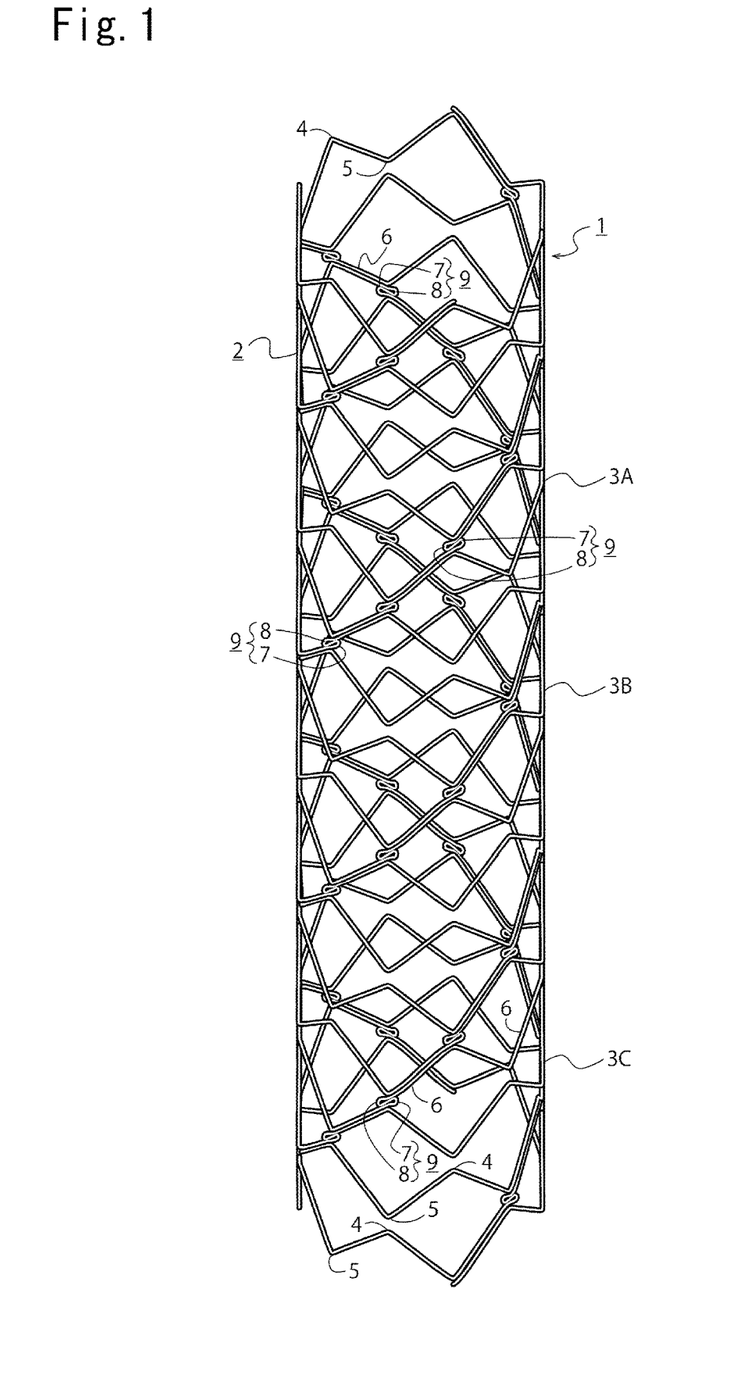
FIG. 1 is a perspective view illustrating a vascular stent according to the present disclosure.
Figure 2:
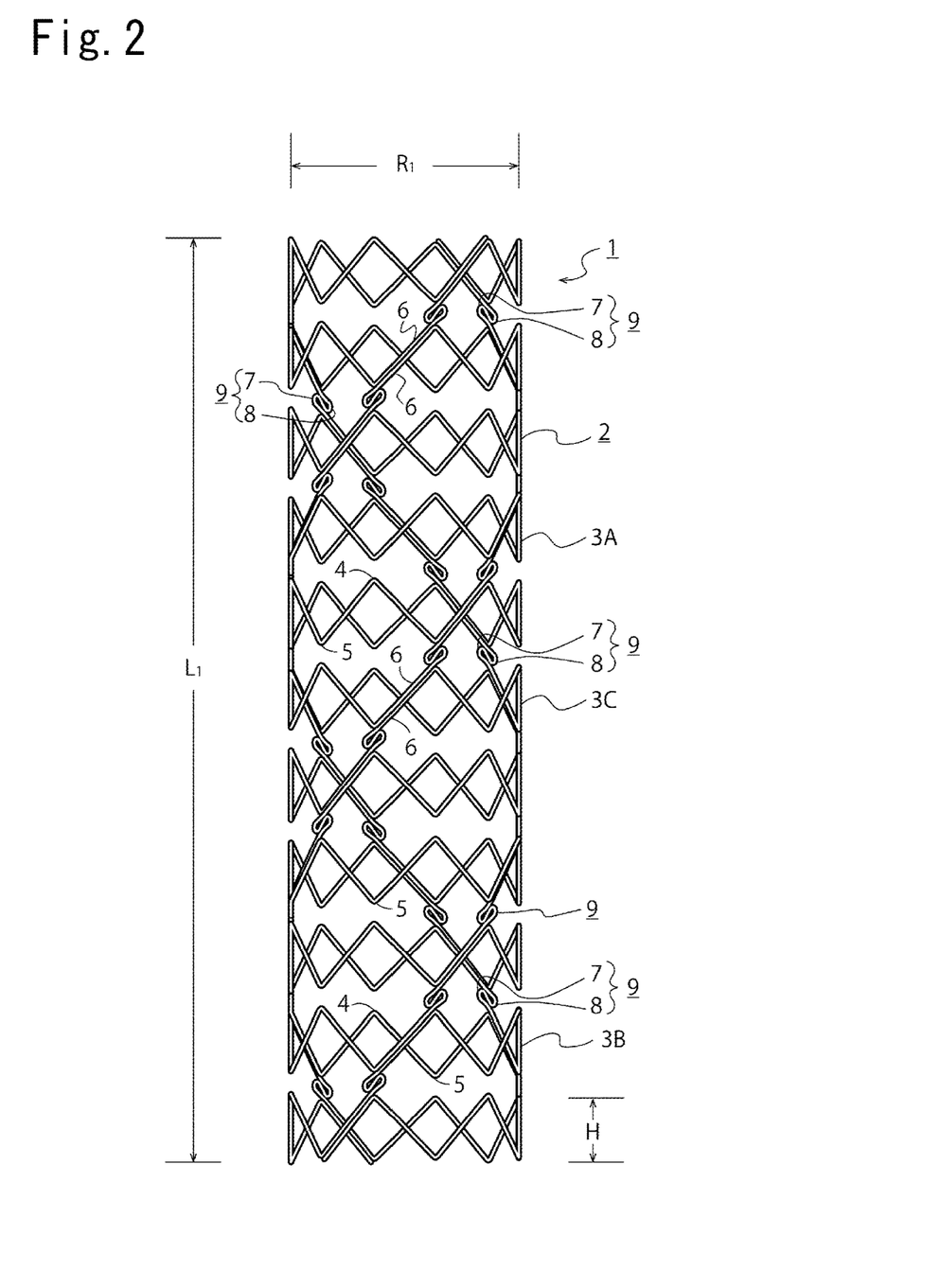
FIG. 2 is a side view illustrating the vascular stent illustrated in FIG. 1.
Figure 3:
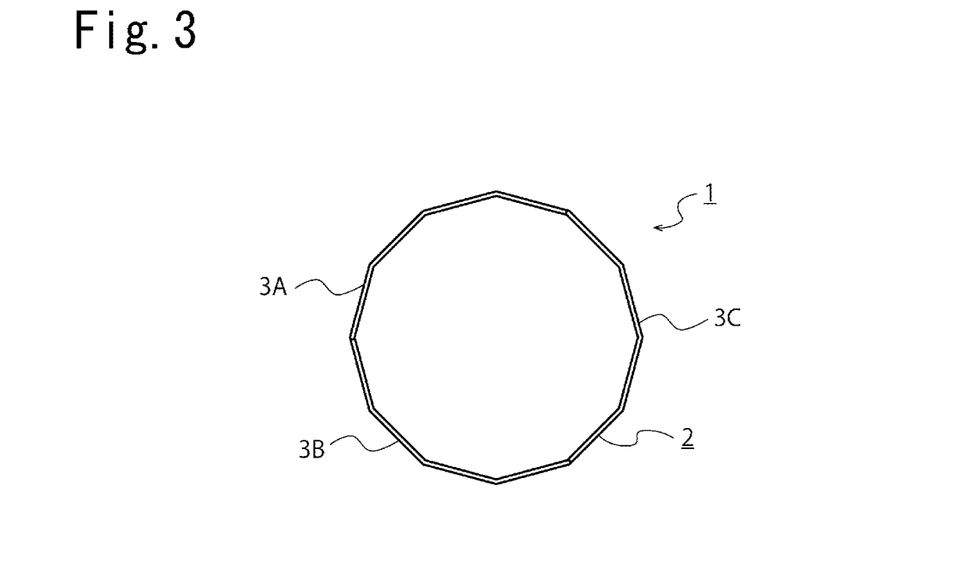
FIG. 3 is a plan view illustrating the vascular stent illustrated in FIG. 1.
Figure 4:
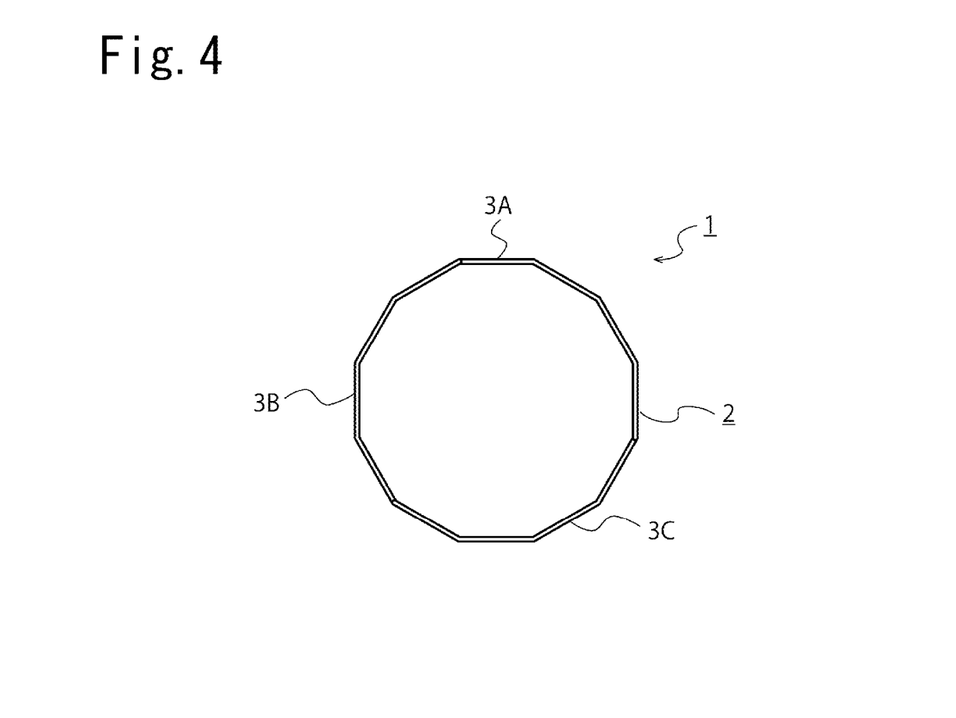
FIG. 4 is a bottom view illustrating the vascular stent illustrated in FIG. 1.

As illustrated in FIGS. 1 and 2, in the first to third tube-forming elements 3A, 3B, 3C thus formed, mutual connecting legs 6, 6 are positioned adjacently to constitute the tube 2 so that the first and second projecting parts 4, 5 are disposed in multiple stages in the axial direction of the tube 2.

It should be noted that a height H (refer to FIG. 2) from minimums to maximums from the first projecting part 4 to the second projecting part 5 formed on each of the tube-forming elements 3A, 3B, 3C may be selected as appropriate according to the size of the vascular stent 1.

Figure 8:
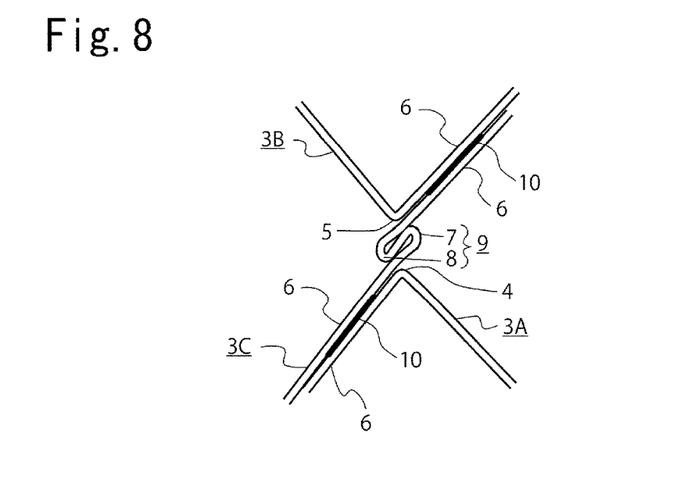
FIG. 8 is an enlarged side view illustrating a portion of the vascular stent illustrated in FIG. 1.

Furthermore, the mutually adjacent connecting legs 6, 6 of the first to third tube-forming elements 3A, 3B, 3C combined with each other to constitute the single tube 2 are integrated by bonding in a portion thereof. The mutually adjacent connecting legs 6, 6 may be bonded by adhesive bonding structures using an adhesive or welded bonding structure such as by using a laser light to melt a portion of the connecting legs 6, 6 to bond them, among others. It should be noted that, as illustrated in FIG. 8, it is sufficient to provide a connecting part 10 for bonding the mutually adjacent connecting legs 6, 6 in only a portion of the length along which the connecting legs 6, 6 are in mutual contact.

Furthermore, when the first to third tube-forming elements 3A, 3B, 3C having the upwardly-bent first projecting part 4 and the downwardly-bent second projecting part 5 formed therein in multiple stages via the connecting leg 6 are combined together to constitute the single tube 2, the mutually adjacent connecting legs 6, 6 are combined in a state in which, as illustrated in FIGS. 1 and 2, the first projecting part 4 and the second projecting part 5 formed in each of the tube-forming elements 3A, 3B, 3C in upper and lower positions are offset at each stage. At this time the elastic displacement member 9, as illustrated in FIG. 8, formed on one of the tube-forming elements 3A, 3B, 3C is disposed between the upwardly-bent first projecting part 4 and the downwardly-bent second projecting part 5 of the other tube-forming elements 3A, 3B, 3C.

Each of the end portions of the tube-forming elements 3A, 3B, 3C combined together to form the single tube 2 of the vascular stent 1 are bonded to an adjacent tube-forming element 3A, 3B, 3C so as to form the end surface of the tube 2 with the single continuous strand.

The tube 2 formed as described above by combining the first to third tube-forming elements 3A, 3B, 3C constitutes the vascular stent 1 having a single flow path. The vascular stent 1 thus formed includes the elastic displacement member 9 comprising the pair of bends 7, 8 disposed in a middle portion of the first and second projecting parts 4, 5 formed in multiple stages to constitute a peripheral wall of the pipe-shaped tube 2.

Moreover, contraction to reduce the outer diameter of the vascular stent 1 according to the present disclosure can be achieved by decreasing the opening angle θ of the first and second projecting parts 4, 5 formed in the first to third tube-forming elements 3A, 3B, 3C.

The contracted vascular stent 1 is guided into a blood vessel mounted to a stent delivery device such as a balloon catheter and implanted at a lesion site within the blood vessel. The vascular stent 1 implanted at the lesion site is then expanded by expanding the balloon to expand and scaffold the blood vessel from the inside.

As described above, irregularly shaped and partially occurring hyperplasia occurs in the stenosed portion within the blood vessel into which the vascular stent 1 is implanted. When the vascular stent 1 is implanted into such a blood vessel having a stenosed site including irregularly shaped and partially occurring hyperplasia, a large load might be applied to portions of the vascular stent 1 causing shape changes thereof.

Figure 9:
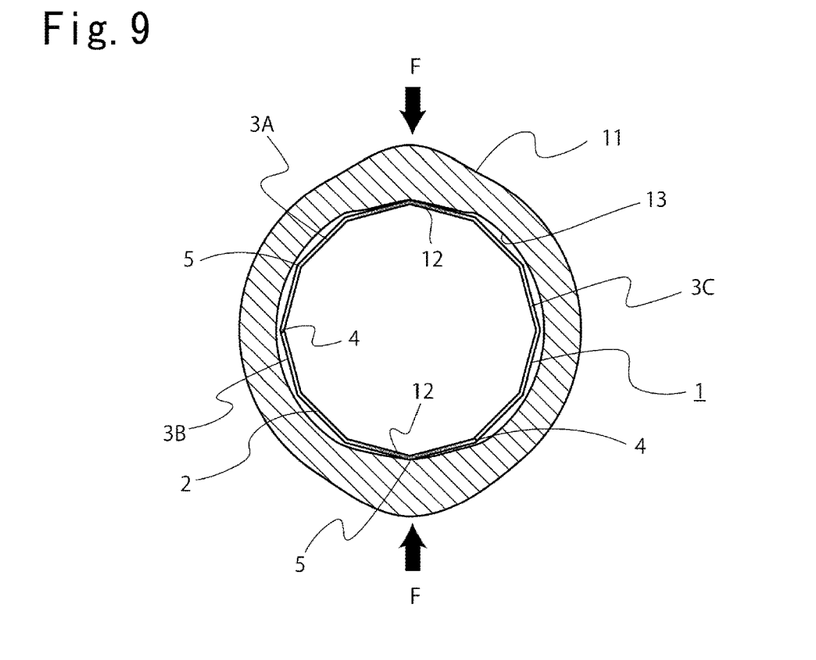
FIG. 9 is a cross-sectional view illustrating a portion of a vascular stent implanted at a stenosed site within a blood vessel in which the vascular stent is deformed by pressure from an irregularly shaped hyperplasia.
Figure 10:
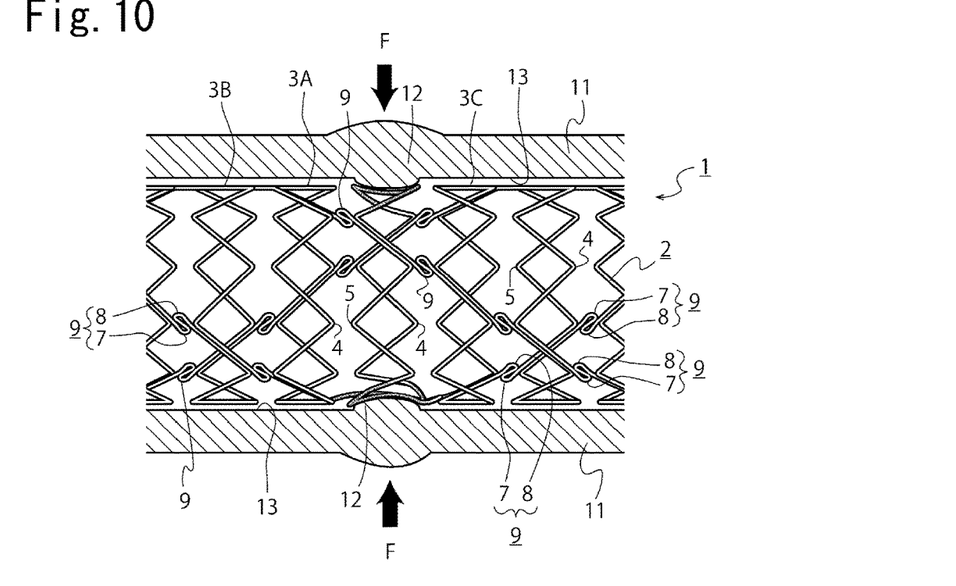
FIG. 10 is a partial side view illustrating a state in which a vascular stent is implanted at a stenosed site within a blood vessel having partial and irregularly shaped hyperplasia.

As illustrated in FIG. 9, the vascular stent 1 according to the present disclosure, when implanted into a blood vessel 11 having a stenosed site including a hyperplasia 12, while pressing the hyperplasia 12 towards the outer perimeter of the blood vessel, expands and scaffolds an inner wall 13 of the blood vessel 11 having a stenosed site. By expanding and scaffolding the inner wall 13 of the blood vessel 11 having a stenosed site with the vascular stent 1, as illustrated in FIG. 10, the vascular stent 1 changes shape to conform to the inner wall 13 of the blood vessel 11 having a stenosed site. Therefore, the inner wall 13 of the blood vessel 11 having a stenosed site is uniformly expanded and scaffolded by the vascular stent 1.

However, when the vascular stent 1 is implanted into the stenosed blood vessel 11 including a hyperplasia 12, a compressing force is applied in a portion thereof by the hyperplasia 12 in the direction F as indicated in FIG. 9. When the first projecting part 4 or the second projecting part 5 are pressed in portions by the hyperplasia 12, the bends 7, 8 situated above and below the first projecting part 4 and the second projecting part 5 are pressed and elastically displaced. Elastic displacement of the bends 7, 8 intercepts transmission of pressing force to the first and second projecting parts 4, 5 that are connected to these bends 7, 8. Therefore, even in the case of a partially and irregularly occurring hyperplasia occurring in the blood vessel targeted for implantation of the vascular stent 1, as illustrated in FIG. 10, while expanding the portion having the hyperplasia 12, the vascular stent 1 changes shape to conform to the inner wall 13 of the blood vessel 11 having the stenosed site and the inner wall 13 of the blood vessel 11 can be uniformly expanded and scaffolded.

As illustrated in FIG. 10, because the vascular stent 1 according to the present disclosure can uniformly expand and scaffold the inner wall 13 of the blood vessel 11 having the stenosed site, occurrence of intimal dissection in the inner wall 13 can be suppressed to achieve a favorable postoperative prognosis.

Furthermore, in the vascular stent 1 according to the present disclosure, when a deforming force is applied in portions to the outer perimeter thereof, the elastic displacement part 9 comprising the bends 7, 8 elastically displace to absorb this deforming force. This thereby prevents application of excessive loads to the connecting part 10 for connecting the mutually adjacent connecting legs 6, 6 of the first to third tube-forming elements 3A, 3B, 3C combined together to constitute the integrated single tube 2 and prevents detachment of this connecting part 10. Furthermore, the vascular stent 1 according to the present disclosure can be maintained in a state of being a single continuous tube over a long-term period after implantation within the blood vessel thereby enabling preservation of an open state within the blood vessel for a predetermined time.

In this embodiment, as illustrated in FIG. 8, when the first to third tube-forming elements 3A, 3B, 3C are combined to constitute the single tube 2, the bends 7, 8 constituting the elastic displacement part 9 are formed so as to curve from the first projecting part 4 of the mutually adjacent first to third tube-forming elements 3A, 3B, 3C, towards the second projecting part 5 side or from the second projecting part 5 towards the first projecting part 4 side. By forming the bends 7, 8 to thus extensively bend so as to project from the mutually adjacent first and second projecting parts 4, 5, elastic displacement capacity of the elastic displacement part 9 can be increased.

Figure 11:
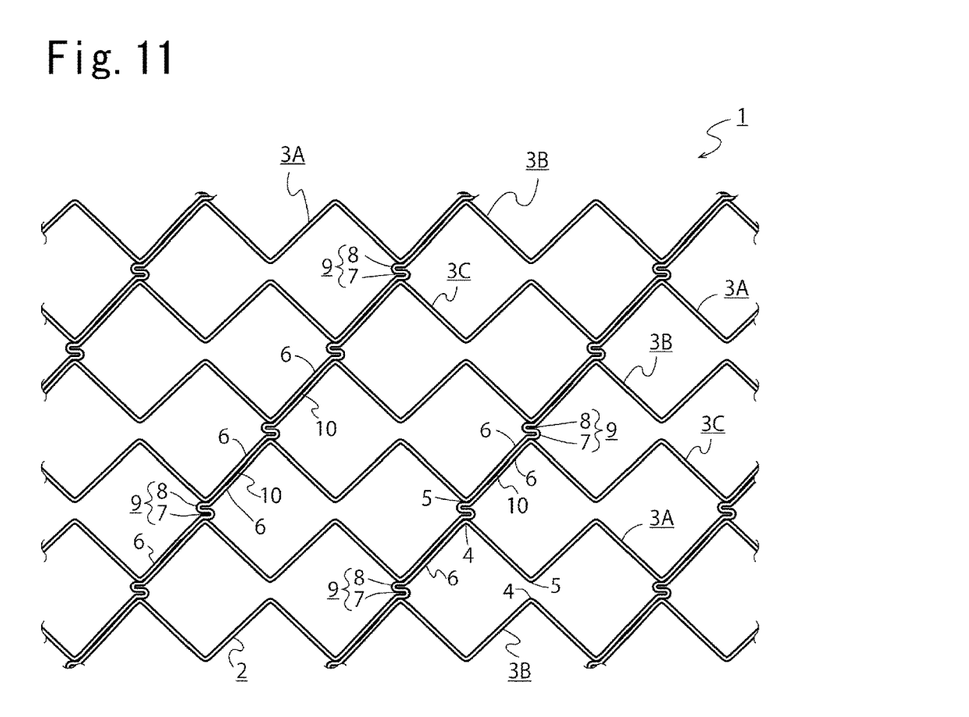
FIG. 11 is a close up schematic view illustrating a portion of a vascular stent according to another embodiment of the present disclosure.

As illustrated in FIG. 11, the bends 7, 8 constituting the elastic displacement part 9 may be formed so as to be mutually separated and in an approximately s-shape. In this case, for example, the elastic displacement part 9 formed in one tube-forming element 3A is formed so as to be disposed between the first projecting part 4 and the second projecting part 5, which are in mutual opposition, of another tube-forming element 3B and yet another tube-forming element 3C constituting the single tube 2.

Figure 12:
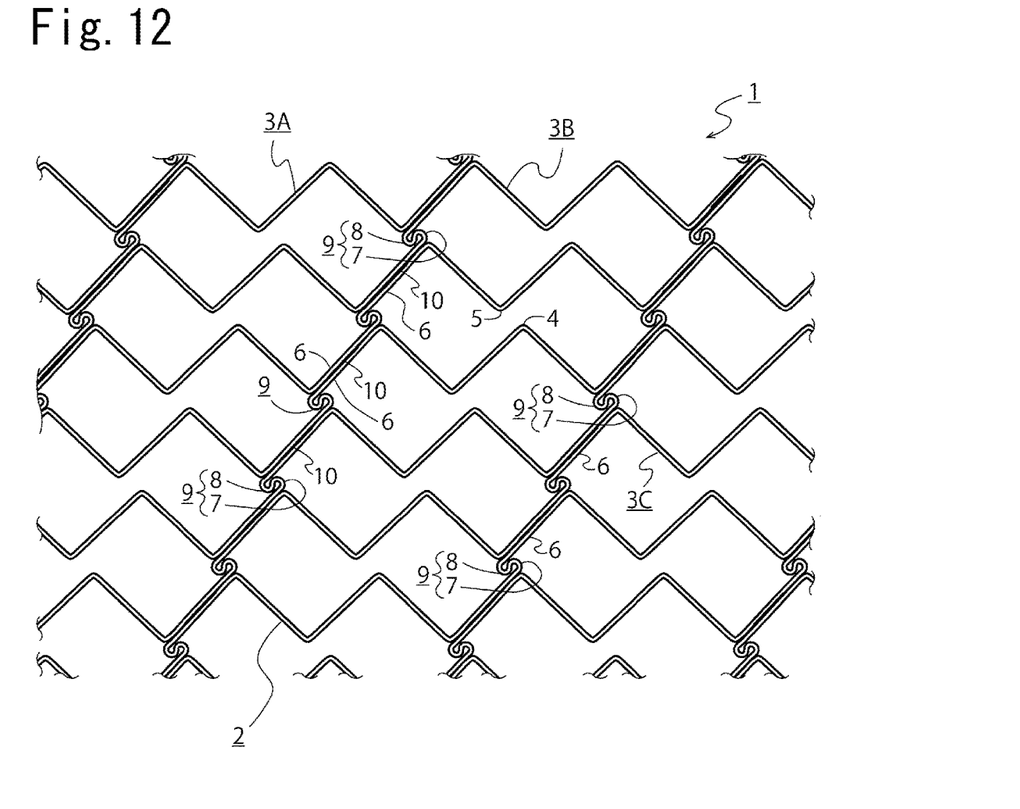
FIG. 12 is a close up schematic view illustrating a portion of a vascular stent according to another embodiment of the present disclosure.

Furthermore, as illustrated in FIG. 12, when the first to third tube-forming elements 3A, 3B, 3C are combined together to form the single tube 2, in the bends 7, 8 constituting the elastic displacement part 9, each of the bends 7, 8 may be formed in a size so as to overlap above the adjacent first and second projecting parts 4, 5.

Size and amount of bending in the bends 7, 8 constituting the elastic displacement part 9 may be selected as appropriate according to strength and thickness of the strand constituting the tube-forming elements 3A, 3B, 3C and, additionally, in consideration of such factors as size of the vascular stent 1.

In the vascular stent 1 according to the present disclosure such as described above, by forming the elastic displacement part 9 for being elastically displaced by a pressing force applied to the tube 2 in a portion of the first to third tube-forming elements 3A, 3B, 3C constituting the single tube 2, even in the case of the blood vessel targeted for implantation having partially occurring and irregularly shaped hyperplasia, the vascular stent 1 changes shape to conform to the inner wall of this blood vessel and can uniformly expand and scaffold the inner wall of the blood vessel.

Furthermore, in the vascular stent 1 according to the present disclosure, by displacement of the elastic displacement part 9 to absorb an externally-originating shape-changing force, loading is prevented from concentrating in the connecting part 10 for connecting the mutually adjacent connecting legs 6, 6 of the first to third tube-forming elements 3A, 3B, 3C and, after implantation within the blood vessel, a state of being a single continuous tube can be maintained over a long-term period.

The above embodiment was described with an example configuration in which the first to third tube-forming elements 3A, 3B, 3C were combined to form the tube 2; however, the vascular stent according to the present disclosure may be formed by combining a pair of tube-forming elements having right/left symmetry. Moreover, a configuration in which four tube-forming elements are combined together may be used. These tube-forming elements are likewise formed with the first and the second projecting parts having an offset in the circumferential direction for each successive stage and the connecting part for connecting each of the tube-forming elements is disposed to succeed in a spiral with an offset in the circumferential direction of the tube.

INDUSTRIAL APPLICABILITY

The vascular stent according to the present disclosure is used as a component for implanting into a living vessel including blood vessels such as a coronary artery, trachea or bile duct to provide support from the inside. Being formed of a biodegradable polymer, the vascular stent dissolves within a living body after the passage of a selected period of time after implantation within the living body.

REFERENCE SIGNS LIST 1 vascular stent, 2 tube, 3A first tube-forming element, 3B second tube-forming element, 3C third tube-forming element, 4 first projecting part, 5 second projecting part, 6 connecting leg, 7, 8 bends, 9 elastic displacement part, 10 connecting part, 11 blood vessel having a stenosed site, 12 hyperplasia, 13 inner wall

What is claimed is:

1. A vascular stent for implanting into a vessel of a living body to scaffold the vessel from the inside thereof, the vascular stent comprising:
    a plurality of tube-forming elements combined with each other to construct a tube constituting a single flow path from one side to another side, the plurality of tube-forming elements each are formed by bending a single continuous strand made of a continuous biodegradable polymer, the plurality of tube-forming elements each comprise a plurality of alternating first projecting parts and second projecting parts, the first projecting parts projecting in a first direction, and the second projecting parts projecting in a second direction opposite to the first direction,
    the plurality of tube-forming elements each comprise a connecting leg connecting a first side of one projecting part and a second side of one second projecting part adjacent to the one first projecting part, the connecting leg comprises an elastic displacement part comprising a first bend, a second bend, a first member extending from the first side of the one first projecting part to the first bend, a second member connecting the first bend and the second bend, and a third member extending from the second side of the one second projecting part to the second bend, a length of the second member is smaller than a length of the first side and a length of the second side, the first bend and the second bend projecting to opposite directions,
    the elastic displacement part is configured such that when a pressing force is applied to the tube, the first bend and the second bend are pressed and elastically displaced, the elastic displacement of the first bend and the second bend intercepts transmission of the pressing force to the one first projecting part and the one second projecting part, so that the one first projecting part and the one second projecting part do not deform,
    the plurality of tube-forming elements are combined by bringing the connecting legs of the plurality of tube-forming elements into mutual adjacency, at least a portion of the mutually adjacent connecting legs are bonded so that the plurality of alternating first projecting parts and the second projecting parts stagger in an axial direction of the tube.

2. The vascular stent according to claim 1, wherein the elastic displacement part is formed by curving a portion of the single continuous strand in an approximately s-shape with no mutual overlap.

3. The vascular stent according to any one of the claims 1 and 2, wherein the strand constituting the tube-forming element is made of one or more biodegradable polymers of polyactic acid (PLA), polyglycolic acid (PGA), copolymer of polyglycolic acid and polyactic acid, polydioxanone, copolymer of trimethylene carbonate and glycolide and copolymer of polyglycolic acid or polylactic acid and ε-caprolactone.

4. The vascular stent according to any one of the claims 1, 2, and 3, wherein the mutually adjacent connecting legs are bonded by an adhesive agent or by spot welding.

5. The vascular stent according to any one of the claims 1, 2, 3, and 4, wherein the first and the second projecting parts of the tube-forming element are used as displacement parts to contract and/or expand the outer diameter of the tube.

6. The vascular stent according to claim 1, wherein the first bend projects along a direction of the second side of the one second projecting part, and the second bend projects along a direction of the first side of the one first projecting part.

* * * * *